US010675245B2

(12) United States Patent
Garcia et al.

(10) Patent No.: US 10,675,245 B2
(45) Date of Patent: Jun. 9, 2020

(54) SUSTAINED RELEASE FORMULATION OF A NON-STEROIDAL ANTI-INFLAMMATORY DRUG

(71) Applicant: PACIRA PHARMACEUTICALS, INC., San Diego, CA (US)

(72) Inventors: Louie Daniel Garcia, San Diego, CA (US); Liangjin Zhu, San Diego, CA (US); William Joseph Lambert, North Potomac, MD (US); Gary Patou, Los Altos Hills, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 547 days.

(21) Appl. No.: 13/787,382

(22) Filed: Mar. 6, 2013

(65) Prior Publication Data
US 2013/0209548 A1 Aug. 15, 2013

Related U.S. Application Data

(63) Continuation of application No. 13/283,450, filed on Oct. 27, 2011.

(60) Provisional application No. 61/407,872, filed on Oct. 28, 2010.

(51) Int. Cl.
A61K 9/127 (2006.01)
A61K 31/5415 (2006.01)
A61K 31/196 (2006.01)
A61K 31/407 (2006.01)

(52) U.S. Cl.
CPC ............ A61K 9/1272 (2013.01); A61K 9/127 (2013.01); A61K 9/1277 (2013.01); A61K 9/1278 (2013.01); A61K 31/196 (2013.01); A61K 31/407 (2013.01); A61K 31/5415 (2013.01)

(58) Field of Classification Search
CPC .............................. A61K 9/127; A61K 9/1271
USPC ...................................................... 424/450
See application file for complete search history.

(56) References Cited

U.S. PATENT DOCUMENTS

| 3,547,119 | A | 12/1970 | Hall et al. |
| 4,311,137 | A | 1/1982 | Gerard |
| 4,531,937 | A | 7/1985 | Yates |
| 4,565,696 | A | 1/1986 | Heath et al. |
| 4,612,370 | A | 9/1986 | Hunt |
| 4,755,173 | A | 7/1988 | Konopka et al. |
| 4,897,355 | A | 1/1990 | Eppstein et al. |
| 4,933,192 | A | 6/1990 | Darling et al. |
| 5,204,112 | A | 4/1993 | Hope et al. |
| 5,230,800 | A | 7/1993 | Park et al. |
| 5,230,899 | A | 7/1993 | Park et al. |
| 5,576,017 | A | 11/1996 | Kim |
| 5,723,147 | A | 3/1998 | Kim et al. |
| 5,759,573 | A | 6/1998 | Kim |
| 5,766,627 | A | 6/1998 | Sankaram et al. |
| 5,962,016 | A | 10/1999 | Willis |
| 5,993,850 | A | 11/1999 | Sankaram et al. |
| 6,017,328 | A | 1/2000 | Fischell et al. |
| 6,106,858 | A | 8/2000 | Ye et al. |
| 6,132,766 | A | 10/2000 | Sankaram et al. |
| 6,162,462 | A | 12/2000 | Bolotin et al. |
| 6,258,791 | B1 | 7/2001 | Braun et al. |
| 6,306,432 | B1 | 10/2001 | Shirley et al. |
| 6,759,057 | B1 | 7/2004 | Weiner et al. |
| 7,105,330 | B2 | 9/2006 | Stern et al. |
| 8,097,614 | B2 * | 1/2012 | Heit ........................ A61K 9/006 514/224.2 |
| 8,182,835 | B2 | 5/2012 | Kim et al. |
| 2002/0009466 | A1 | 1/2002 | Brayden |
| 2002/0035107 | A1 | 3/2002 | Henke |
| 2002/0039596 | A1 | 4/2002 | Hartounian et al. |
| 2002/0169102 | A1 | 11/2002 | Frey, II |
| 2003/0060559 | A1 | 3/2003 | Oliviere et al. |
| 2003/0162234 | A1 | 8/2003 | Jallad et al. |
| 2003/0235610 | A1 | 12/2003 | McLean et al. |
| 2004/0071767 | A1 | 4/2004 | Cevc et al. |
| 2004/0171740 | A1 | 9/2004 | Ruberti et al. |
| 2004/0224010 | A1 * | 11/2004 | Hofland et al. ................ 424/450 |
| 2004/0268425 | A1 | 12/2004 | Bookbinder et al. |
| 2005/0268425 | A1 | 12/2005 | Clemons, Sr. |
| 2005/0272697 | A1 | 12/2005 | Herzberg et al. |
| 2006/0104968 | A1 | 5/2006 | Bookbinder et al. |

(Continued)

FOREIGN PATENT DOCUMENTS

| CN | 101744764 | 6/2010 |
| EP | 0280503 | 4/1993 |

(Continued)

OTHER PUBLICATIONS

Bangham, et al., "Diffusion of Univalent Ions across the Lamellae of Swollen Phospholipids", J. Mol. Biol., (1965)13:238-252.
Bannwarth, et al., "Piroxicam concentrations in plasma and synovial fluid after a single dose of piroxicam-β-cyclodextrin", International Journal of Clinical Pharmacology and Therapeutics, (2001) 39(1):33-36.
Bardou, et al., "Preventing the gastrointestinal adverse effects of nonsteroidal anti-inflammatory drugs: From risk factor identification to risk factor intervention", Joint Bone Spine, (2010) 77(1):6-12.

(Continued)

Primary Examiner — Gollamudi S. Kishore
(74) Attorney, Agent, or Firm — Knobbe, Martens, Olson & Bear, LLP

(57) ABSTRACT

Disclosed are formulations comprising multivesicular liposomes and one or more non-steroidal anti-inflammatory drugs which minimize the side effects of unencapsulated non-steroidal anti-inflammatory drugs while maintaining or improving efficacy. Methods of making and administering the formulations comprising multivesicular liposomes and one or more non-steroidal anti-inflammatory drugs and their use as medicaments are also provided.

19 Claims, No Drawings

(56) References Cited

U.S. PATENT DOCUMENTS

| | | | |
|---|---|---|---|
| 2007/0009434 | A1 | 1/2007 | Low et al. |
| 2007/0009583 | A1 | 1/2007 | Qvist |
| 2007/0065541 | A1 | 3/2007 | Keller et al. |
| 2007/0116777 | A1 | 5/2007 | Schwarz et al. |
| 2007/0232566 | A1 | 10/2007 | Wright et al. |
| 2007/0235889 | A1 | 10/2007 | Hartounian et al. |
| 2008/0075807 | A1 | 3/2008 | Baldwin et al. |
| 2008/0090861 | A1 | 4/2008 | Barrett |
| 2009/0131543 | A1 | 5/2009 | Weitz et al. |
| 2009/0232731 | A1 | 9/2009 | Funk et al. |
| 2009/0269396 | A1 | 10/2009 | Cipolla et al. |
| 2009/0291133 | A1 | 11/2009 | Wang et al. |
| 2009/0311237 | A1 | 12/2009 | Frost |
| 2010/0035937 | A1* | 2/2010 | Gruber ............... A61K 9/143 514/352 |
| 2010/0056403 | A1* | 3/2010 | Abad ............... C08B 15/005 507/214 |
| 2010/0119592 | A1 | 5/2010 | Frankel |
| 2011/0142917 | A1 | 6/2011 | Alpert et al. |
| 2011/0237648 | A1* | 9/2011 | Khvorova ............. C12N 15/111 514/44 A |
| 2011/0250264 | A1 | 10/2011 | Schutt et al. |
| 2012/0027842 | A1 | 2/2012 | Hutchinson et al. |
| 2012/0128757 | A1 | 5/2012 | Kikuchi et al. |
| 2012/0244206 | A1* | 9/2012 | Cipolla et al. ............ 424/450 |
| 2015/0174069 | A1 | 6/2015 | Hong et al. |
| 2015/0231069 | A1 | 8/2015 | Modi |
| 2015/0265867 | A1 | 9/2015 | Sarangapani |

FOREIGN PATENT DOCUMENTS

| | | |
|---|---|---|
| JP | 01-125318 | 5/1989 |
| JP | 02-502907 | 9/1990 |
| JP | 08-509230 | 10/1996 |
| JP | 2005-536481 | 12/2005 |
| JP | 2010-507658 | 3/2010 |
| WO | WO 87/07506 | 12/1987 |
| WO | WO 88/07853 | 10/1988 |
| WO | WO 92/09268 | 6/1992 |
| WO | WO 94/23697 | 10/1994 |
| WO | WO 96/08235 | 3/1996 |
| WO | WO 1999/025319 A1 | 5/1999 |
| WO | WO 03/020037 A1 | 3/2003 |
| WO | WO 2003/046145 | 6/2003 |
| WO | WO 2004/000226 | 12/2003 |
| WO | WO 07/049278 | 5/2007 |
| WO | WO 2008/030818 A2 | 3/2008 |
| WO | WO 2008/063341 | 5/2008 |
| WO | WO 08/072952 | 6/2008 |
| WO | WO 2010/014895 | 2/2010 |
| WO | WO 2010/113983 | 10/2010 |

OTHER PUBLICATIONS

Barnard, et al., "Increase in Nonfatal Digestive Perforations and Haemorrhages Following Introduction of Selective NSAIDs", *Drug Safety*, (2006); 29(7):613-20.

Bjorkman, "Current Status of Nonsteroidal Anti-Inflammatory Drug (NSAID) Use in the United States: Risk Factors and Frequency of Complications", *Am. J. Med.*, (1999) 107(6A):3S-10S.

Cullis, et al., *"Liposomes as Pharmaceuticals"*, (Ostro, Ed.), Marcel Deker Inc., (1987) 60-65.

Foong, et al., "Retention and Distribution of Liposome-entrapped [$^3$H]Methotrexate Injected into Normal or Arthritic Rabbit Joints", *J. Pharm. Pharmacol.*, (1988) 40:464-468.

Foong, et al., "Treatment of Antigen-induced Arthritis in Rabbits with Liposome-entrapped Methotrexate Injected Intra-articularly", *J. Pharm. Pharmacol.*, (1993) 45:204-209.

Fowler, "Plasma and Synovial Fluid Concentrations of Diclofenac Sodium and Its Hydroxylated Metabolites During Once-Daily Administration of a 100 mg Slow-Release Formulation", *Eur. J. Clin. Pharmacol.*, (1986) 31:469-472.

Hollenz, et al., "NSAID-Associated Dyspepsia and Ulcers: A prospective Cohort Study in Primary Care", *Digestive Diseases*, (2006) 24:189-194.

Huang, "Studies on Phosphatidylcholine Vesicles. Formation and Physical Characteristics", *Biochemistry*, (1969) 8(1):334-352.

Hundal, et al., "Total and Free Plasma and Total Synovial Fluid Piroxicam Concentrations: Relationship to Antiinflammatory Effect in Patients with Reactive Arthritis and Other Arthritides", *Scand. J. Rheumatol.*, (1993) 22(4):183-187.

Hwang, et al., "Remote loading of diclofenac, insulin and fluorescein isothiocyanate labeled insulin into liposomes by pH and acetate gradient methods", *Int. J. Pharm.*, (1999) 179:85-95.

Kim, et al., "Preparation of Cell-Size Unilamellar Liposomes With High Captured Volume and Defined Siz", *Biochimica et Biophysica Acta*, (1981) 646(1):1-9.

Kim, et al., "Preparation of Multivesicular Liposomes", *Biochimica et Biophysica Acta*, (1983) 728: 339-348.

Larsen, et al., "Intra-Articular Depot Formulation Principles: Role in the Management of Postoperative Pain and Arthritic Disorders", *J. Pharm. Sci.*, (2008) 97(11):4622-4654.

Neander, et al., "Pharmacokinetics of intraarticular indomethacin in patients with osteoarthritis", *Eur. J. Clin. Pharmacol.*, (1992) 42(3):301-305.

Peris, et al., "Iatrogenic Cost Factors Incorporating Mild and Moderate Adverse Events in the Economic Comparison of Aceclofenac and Other NSAIDs", *Pharmacoeconomics*, (2001)19(7):779-790.

Shibuya, et al., "Colonic mucosal lesions associated with long-term or short-term administration of nonsteroidal anti-inflammatory drugs ", *Colorectal Diseases*, (2009) 12:1113-1121.

Yamagata, et al., "Prevalence and incidence of NSAID-induced gastrointestinal ulcers and bleeding", *Nippon Rinsho*, (2007) 65(10):1749-1753.

Zhang, "STEALTH Liposomes: the silent nanobombers", *Trends in Bio/Pharm. Ind.*, (2008)4:19-24.

International Search Report and Written Opinion dated Mar. 7, 2012, for International Application No. PCT/US/11/58169, filed Oct. 27, 2011.

Jain et al., Multivesicular liposomes bearing celecoxib-beta-cyclodextrin complex for transdermal delivery, Drug Deliv. (Aug. 2007)14(6):327-35.

Xu Shi Ying, Microencapsulation Technology: Principles and Applications, Beijing Chemical Industry Press (2006), ISBN 7-5025-8870-1.

Fricker et al., Phospholipids and lipid-based formulations in oral drug delivery, Pharmaceutical Research, 27:1469-1486, Aug. 2010.

Mantripragada, 2002, A lipid based depot (DepoFoam® technology) for sustained release drug delivery, Progress in Lipid Research 41:392-406.

Patel et al., Chapter 25. Pain Management, in Desai et al. eds., Gibaldi's Drug Delivery Systems in Pharmaceutical Care, 2007, p. 469.

Martin et al., 1993, Physical Pharmacy, Fourth Edition, Lippincott Williams & Wilkins, Baltimore, MD, p. 101.

Definition of Instillation, Dorland's Illustrated Medical Dictionary, W.B. Saunders Company, Philadelphia, PA, p. 904.

Extended European Search Report dated Jun. 17, 2016 in related European patent application No. 11837126.9.

* cited by examiner

SUSTAINED RELEASE FORMULATION OF A NON-STEROIDAL ANTI-INFLAMMATORY DRUG

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation application, and claims the benefit of priority to U.S. patent application Ser. No. 13/283,450, entitled "A SUSTAINED RELEASE FORMULATION OF A NON-STEROIDAL ANTI-INFLAMMATORY DRUG," filed Oct. 27, 2011, which claims the benefit of priority to U.S. Provisional Application Ser. No. 61/407,872, filed Oct. 28, 2010, each of which is hereby incorporated by reference in its entirety.

BACKGROUND OF THE INVENTION

Field of the Invention

The present application relates to multivesicular liposome (MVL) formulations of non-steroidal anti-inflammatory drugs (NSAIDs) which minimize the side effects of NSAIDs while maintaining or improving efficacy. In particular, embodiments of the invention relate to compositions comprising NSAIDs and multivesicular liposomes, and methods of administration of the same. Methods of making multivesicular liposomes containing an NSAID and their use as medicaments are also provided.

Background Information

NSAID compounds, administered orally, are effective relievers of pain and inflammation in a variety of therapeutic settings. Because of their effectiveness, the use of oral NSAIDs for the treatment of acute and chronic joint pain and inflammation is growing rapidly (Bjorkman, *Am. J. Med.*, 107(6A):3S-10S (1999); Barnard et al., *Drug Safety*, 29(7): 613-20 (2007); Bardou et al., *Joint Bone Spine*, 77(1):6-12 (2010)). NSAIDs are also widely used for the treatment of post-operative pain, typically administered either intravenously or orally. Oral NSAID treatment, however, has been linked to a variety of serious gastrointestinal complications, including peptic ulcer, digestive perforation, hemorrhage, colonic ulcer, and colitis (Hollenz et al., *Dig Dis.*, 24(1-2): 189-94 (2006); Yamagata et al., *Nippon Rinsho*, 65(10): 1749-53 (2007); Shibuya et al., *Colorectal Dis.* (2009)). Gastro-intestinal (GI) symptoms can appear within the first two weeks of therapy. Therefore, patients with both acute and chronic conditions are affected (Penis et al., *Pharmacoeconomics*, 19(7):779-90 (2001)). GI toxicity, and the increased morbidity that results from it, account for the majority of the cost associated with NSAID therapy (Id). It threatens both the utility and economic viability of NSAID therapy for the treatment of pain and inflammation (Bjorkman, *Am. J. Med.*, 107(6A):3S-10S (1999)). Gastro-protective co-therapy is being explored as a solution to the GI toxicity problem; however this approach is currently considered cost prohibitive (Id.).

In general, GI toxicity is attributable to the magnitude and duration of drug exposure both in the GI tract following oral dosing and with high systemic levels of drug required to achieve efficacious drug levels at the synovial site of action. The key to improving the efficacy of NSAID therapy and to reducing GI or opioid-related side effects is to develop a treatment that provides efficacious and prolonged levels of drug directly to the joint synovial cavity or surgical wound without GI or high systemic exposure. Effective NSAIDs such as diclofenac (DCF), meloxicam (MLX) and piroxicam (PRX) are typically systemically administered at doses of 100-150 mg/day, 7.5-15 mg/day, and 20 mg/day, respectively. These relatively high, side effect-inducing doses are necessary to achieve efficacious drug levels in the synovial cavity or wound site. The levels of drug achieved in the synovial cavity following systemic NSAID administration have been shown to be significantly lower than that of plasma (Bannwart et al., *Int. J. Clin. Pharmacol. Therapy*, 39(1):33-36 (2001); Hundal et al., *Scand. J. Rheumatol.*, 22(4):183-187 (1993)). Chronic 100 mg/day systemic dosing of diclofenac, for instance, produces efficacious synovial fluid levels of 200 ng/mL or less. In a 25 mL synovial space (this volume would represent a diseased knee; normal volume is 2 mL), this corresponds to an intraarticular dose of approximately 5 µg, a dose easily achieved with formulations described in this herein (Fowler, *Eur. J. Clin. Pharmacol.*, 31(4):469-472 (1986)). For more potent NSAIDs such as MLX and PRX, the synovial drug concentrations required for efficacy are expected to be much lower.

The local residence time of drug in the synovial cavity is closely related to drug efficacy (Foong et al., *J. Pharm. Pharmacol.*, 40(7):464-468 (1988); Foong et al., *J. Pharm. Pharmacol.*, 45(3):204-209,15 (1993)). However, drugs are typically cleared in a matter of hours from the synovial fluid (Neander et al., *Eur. J. Clin. Pharmacol.*, 42(3):301-305 (1992); Larsen et al., *J. Pharm. Sci.*, 97(11):4622-4654 (2008)). Single doses of unencapsulated NSAID drugs, therefore, whether they are administered intraarticularly or orally, have limited opportunity to achieve their therapeutic effect.

Methods of making liposomes encapsulating therapeutic agents, none has been described in Hwang et al., *Int. J. Pharm.* 179(1):85-95 (1999); (Cullis et al., 1987, in Liposomes from Biophysics to Therapeutics (Ostro, Ed.), Marcel Deker Inc., pp. 60-65); and (Zhang, *Trends in Bio/Pharm. Ind.*, 4:19-24 (2008)).

The instant formulations and methods address the shortcomings of current NSAID therapy and formulations and provide other advantages as well.

SUMMARY OF THE INVENTION

The present embodiments provide a formulation of one or more non-steroidal anti-inflammatory drugs, comprising one or more non-steroidal anti-inflammatory drugs; and multivesicular liposomes, wherein the one or more non-steroidal anti-inflammatory drugs are encapsulated in the multivesicular liposomes. In some embodiments, the one or more non-steroidal anti-inflammatory drugs is chosen from the group consisting of indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin. piroxicam, meloxicam, ampiroxicam, droxicam, pivoxicam, lornoxicam, cinnoxicam, sudoxicam, and tenoxicam.

In other embodiments the multivesicular liposomes further comprise cholesterol, one or more phospholipids, including salts of the phospholipids, and one or more triglycerides. In certain embodiments, the phospholipid is a phosphatidyl choline, a phosphatidyl glycerol and salts thereof, or a combination of these. In further embodiments, the phosphatidyl glycerol is DPPG. In an additional embodiment, the phosphatidyl choline is DEPC. In an additional embodiment, the phosphatidyl choline is DOPC. In some embodiments, the triglyceride is triolein, tricaprylin, or a combination of the two.

In another embodiment, the multivesicular liposomes further comprise a pH modifier. In an additional embodiment, the pH modifier is lysine or glutamic acid, or a combination thereof. In further embodiments, the pH modifier can be an organic acid, an inorganic acid, an organic base, or an inorganic base.

In further embodiments, the multivesicular liposomes further comprise a cyclodextrin. In some embodiments, the cyclodextrin is in a concentration of from about 10 mg/ml to about 400 mg/ml complexed with the non-steroidal anti-inflammatory drug within the multivesicular liposomes. In certain embodiments, the cyclodextrin is selected form the group consisting of (2,6-Di-O-)ethyl-β-cyclodextrin, (2-Carboxyethyl)-β-cyclodextrin sodium salt, (2-hydroxyethyl)-β-cyclodextrin, (2-hydroxypropyl)-α-cyclodextrin, sulfobutylether-β-cyclodextrin, (2-hydroxypropyl)-β-cyclodextrin, 6-monodeoxy-6-monoamino-β-cyclodextrin, 6-β-α-maltosyl-β-cyclodextrin, butyl-β-cyclodextrin, butyl-γ-cyclodextrin, carboxymethyl-β-cyclodextrin, methyl-β-cyclodextrin, succinyl-α-cyclodextrin, succinyl-β-cyclodextrin, triacetyl-β-cyclodextrin, α-cyclodextrin β-cyclodextrin, and γ-cyclodextrin.

Another embodiment provides a method of treating pain and inflammation, comprising injecting NSAID-MVL formulations described herein into a subject in need thereof. In some embodiments, the one or more non-steroidal anti-inflammatory drugs are chosen from the group consisting of indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, pivoxicam, lornoxicam, cinnoxicam, sudoxicam, and tenoxicam. In other embodiments, the formulations of the method include a pharmaceutically acceptable carrier for injection.

In further embodiments, the multivesicular liposomes further comprise cholesterol, one or more phospholipids, including salts of the phospholipid, and one or more triglycerides. In other embodiments, the multivesicular liposomes further comprise DPPG, DEPC, DOPC, tricaprylin, lysine, glutamic acid, and combinations thereof.

In some embodiments, the administration can be subcutaneous injection. In certain embodiments, administration can be intramuscular injection. In other embodiments, administration can be intraarticular injection. In some embodiments, the administration is directly infiltrated by local injection into the wound margin or instillation into the incision wound, or a combination thereof following surgery. In some embodiments, administration is topical. In some embodiments, topical administration can be ocular, nasal, or otic. In other embodiments, administration is intraocular. In additional embodiments, the administration is every 1 to 7 days.

Another embodiment provides a process for preparing multivesicular liposomal formulations, the process comprising providing a first emulsion by mixing a first aqueous phase and a volatile water-immiscible solvent phase, said solvent phase comprising at least one amphipathic lipid and at least one neutral lipid, mixing and emulsifying said first emulsion and a second aqueous phase to provide a second emulsion, said second emulsion comprising a continuous aqueous phase, removing the volatile water-immiscible solvent from the second emulsion to form a composition of blank multivesicular liposomal particles; remote loading a non-steroidal anti-inflammatory drug(s) into said multivesicular liposomes, wherein a gradient of low pH outside the MVL to high pH inside the MVL is present to drive the NSAID into the MVL.

In some embodiments, the multivesicular liposomes further comprise a pH modifier. In further embodiments, the pH modifier is lysine or glutamic acid, or a combination thereof. In other embodiments, the pH modifier can be an organic acid, an inorganic acid, an organic base, an inorganic base, or a combination thereof. In additional embodiments, the glutamic acid is adjusted to a pH from about 4.7 to about 9.2. In some embodiments, the pH gradient is from about 1 to about 2 pH units.

In one embodiment, the non-steroidal anti-inflammatory drug can be diclofenac. In another embodiment, the non-steroidal anti-inflammatory drug can be piroxicam. In another embodiment, the non-steroidal anti-inflammatory drug can be meloxicam. In another embodiment, the non-steroidal anti-inflammatory drug can be ketorolac.

Another embodiment provides a process for preparing multivesicular liposomal formulations, the process comprising providing a first emulsion by mixing at least one NSAID, a first aqueous phase and a volatile water-immiscible solvent phase, said solvent phase comprising at least one amphipathic lipid and at least one neutral lipid, mixing and emulsifying said first emulsion and a second aqueous phase to provide a second emulsion, said second emulsion comprising a continuous aqueous phase, removing the volatile water-immiscible solvent from the second emulsion to form a composition of blank multivesicular liposomal particles. In some embodiments, the NSAID is added to the first aqueous solution prior to mixing. In some embodiments, the NSAID is added to the volatile water-immiscible solvent phase prior to mixing. In some embodiments, the NSAID is added to both the first aqueous solution and volatile water-immiscible solvent phase prior to mixing.

In some embodiments, the multivesicular liposomes further comprise a pH modifier. In further embodiments, the pH modifier is lysine or glutamic acid, or a combination thereof. In other embodiments, the pH modifier can be an organic acid, an inorganic acid, an organic base, an inorganic base, or a combination thereof.

In some embodiments, the non-steroidal anti-inflammatory drug is diclofenac. In some embodiments, the non-steroidal anti-inflammatory drug is piroxicam. In some embodiments, the non-steroidal anti-inflammatory drug is meloxicam. In some embodiments, the non-steroidal anti-inflammatory drug is ketorolac.

Another embodiment provides the instant multivesicular liposomal formulations prepared by a process comprising, providing a volume of first emulsion by mixing a first aqueous phase and a volatile water-immiscible solvent phase, said solvent phase comprising at least one amphipathic lipid and at least one neutral lipid, providing a volume of second emulsion comprising a continuous aqueous phase by mixing and emulsifying said first emulsion and a second aqueous phase, removing the volatile water-immiscible solvent from the second emulsion to form a composition of multivesicular liposomal particles; and remote loading a non-steroidal anti-inflammatory drug into said multivesicular liposomes, wherein a gradient of low pH outside the MVL to high pH inside the MVL is present to drive the NSAID into the MVL. In some embodiments, the multivesicular liposomes further comprise a pH modifier. In further embodiments, the pH modifier is lysine or glutamic acid, or a combination thereof. In other embodiments, the pH modifier can be an organic acid, an inorganic acid, an organic base, and an inorganic base, or a combination thereof. In additional embodiments, the glutamic acid is adjusted to a pH from about 4.7 to about 9.2. In some embodiments, the pH gradient is from about 1 to about 2 pH. In some embodiments, the non-steroidal anti-inflammatory drug is diclofenac. In some embodiments, the non-steroidal anti-inflammatory drug can be piroxicam. In some embodiments, the non-steroidal anti-inflammatory drug can be meloxicam. In some embodiments, the non-steroidal anti-inflammatory drug can be ketorolac.

Another embodiment provides the instant multivesicular liposomal formulations prepared by a process comprising providing a volume of first emulsion by mixing at least one NSAID, a first aqueous phase and a volatile water-immiscible solvent phase, said solvent phase comprising at least one amphipathic lipid and at least one neutral lipid, providing a volume of second emulsion comprising a continuous aqueous phase by mixing and emulsifying said first emulsion and a second aqueous phase, and removing the volatile water-immiscible solvent from the second emulsion to form a composition of multivesicular liposomal particles. In some embodiments, the NSAID is added to the first aqueous solution prior to mixing. In some embodiments, the NSAID is added to the volatile water-immiscible solvent phase prior to mixing. In some embodiments, the NSAID is added to both the first aqueous solution and volatile water-immiscible solvent phase prior to mixing. In some embodiments, the multivesicular liposomes further comprise a pH modifier. In further embodiments, the pH modifier is lysine or glutamic acid, or a combination thereof. In other embodiments, the pH modifier can be an organic acid, an inorganic acid, an organic base, and an inorganic base, or a combination thereof. In some embodiments, the non-steroidal anti-inflammatory drug is diclofenac. In some embodiments, the non-steroidal anti-inflammatory drug is piroxicam. In some embodiments, the non-steroidal anti-inflammatory drug is meloxicam. In some embodiments, the non-steroidal anti-inflammatory drug is ketorolac.

Another embodiment provides a method of treating pain and inflammation for an extended period of time by wound infiltration, comprising administering a multivesicular liposome (MVL) formulation by local injection into a wound margin, or instillation into an incision wound, or a combination thereof, wherein the formulation comprises one or more non-steroidal anti-inflammatory drugs and multivesicular liposomes, wherein the one or more non-steroidal anti-inflammatory drugs are encapsulated in the multivesicular liposomes. In some embodiments, the non-steroidal anti-inflammatory drug is chosen from the group consisting of indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, pivoxicam, lornoxicam, cinnoxicam, sudoxicam, and tenoxicam.

In one embodiment, the non-steroidal anti-inflammatory drug is diclofenac. In another embodiment, the non-steroidal anti-inflammatory drug is piroxicam. In another embodiment, the non-steroidal anti-inflammatory drug is meloxicam. In another embodiment, the non-steroidal anti-inflammatory drug is ketorolac.

In some embodiments, the multivesicular liposomes further comprise cholesterol, one or more phospholipids, including salts of the phospholipids, and one or more triglycerides. In some embodiments, the phospholipid is a phosphatidyl choline, a phosphatidyl glycerol and salts thereof, or a combination thereof. In one embodiment, the phosphatidyl glycerol is DPPG. In another embodiment, the phosphatidyl choline is DEPC. In another embodiment, the triglyceride is triolein, tricaprylin, or a combination of the two.

In some embodiments, the multivesicular liposomes further comprise a pH modifier. In further embodiments, the pH modifier is lysine or glutamic acid, or a combination thereof. In other embodiments, the pH modifier can be an organic acid, an inorganic acid, an organic base, an inorganic base, or a combination thereof.

In some embodiments, the multivesicular liposomes further comprise a cyclodextrin. In further embodiments, the cyclodextrin is in a concentration of from about 10 mg/ml to about 400 mg/ml complexed with the non-steroidal anti-inflammatory drug within the multivesicular liposomes. In certain embodiments, the cyclodextrin is selected from the group consisting of (2,6-Di-O-)ethyl-β-cyclodextrin, (2-Carboxyethyl)-β-cyclodextrin sodium salt, (2-hydroxyethyl)-β-cyclodextrin, (2-hydroxypropyl)-α-cyclodextrin, sulfobutylether-β-cyclodextrin, (2-hydroxypropyl)-β-cyclodextrin, 6-monodeoxy-6-monoamino-β-cyclodextrin, 6-O-α-maltosyl-β-cyclodextrin, butyl-β-cyclodextrin, butyl-γ-cyclodextrin, carboxymethyl-β-cyclodextrin, methyl-β-cyclodextrin, succinyl-α-cyclodextrin, succinyl-β-cyclodextrin, triacetyl-β-cyclodextrin, α-cyclodextrin β-cyclodextrin, and γ-cyclodextrin.

DETAILED DESCRIPTION OF THE INVENTION

The present embodiments provide formulations comprising multivesicular liposomes (MVLs) containing an amount of one or more NSAIDs which minimize the side effects of NSAIDs while maintaining or improving efficacy (hereinafter NSAID-MVL formulations). The use of NSAID-MVL formulations in the instant embodiments results in the release of NSAIDs for treatment of pain and inflammation for an extended period.

Intraarticular administration of the instant NSAID-MVL formulations addresses all of the above-mentioned shortcomings of current NSAID therapy by delivering drug directly to the site of action, reducing the plasma drug concentration and concentration-dependent side effects, and prolonging the drug exposure of the affected joint from hours to days or weeks, to achieve increased therapeutic benefit. The instant embodiments are useful for acute treatment due to injury, flare-up, or surgery, as well as for chronic conditions such as rheumatoid arthritis (RA) or osteoarthritis (OA) where the inflammation is localized to a limited number of joints. The instant sustained-release NSAID-MVL formulations provide pain relief and reduce inflammation while circumventing the side effects associated with current oral therapy. Using multivesicular liposome sustained-release technology, NSAID-MVL formulations can be administered directly to the affected joint or infiltrated by local injection into the wound margins or instilled into the incision wound following surgery. The instant NSAID-MVL formulations can also be administered by other routes of administration to treat local inflammation or pain. Local administration would include topical, ocular, intraocular, nasal, and otic delivery. Local administration reduces the dose requirement significantly, thereby reducing the potential for gastric and systemic toxicities associated with oral NSAID administration. The instant NSAID-MVL formulations release drug up to two weeks, so patients require infrequent dosing.

Post-surgical wound infiltration of the instant NSAID-MVL formulation also allows for a reduction in the use of opioids and therefore a reduction in opioid-related side effects. Direct injection or instillation of NSAID-MVL into the surgical site can enhance the local action of NSAID by increasing the local tissue concentration while reducing the overall NSAID dosing typically used in post-surgery.

Subcutaneous or intramuscular administration of the instant NSAID-MVL formulations also allow for systemic treatment of pain as an alternative to oral therapy. The advantage of this approach is that the MVL formulation can provide a flatter pharmacokinetic profile than that from oral immediate release dosage forms. Thus, subcutaneous or intramuscular administration provides longer duration and decreased plasma concentration-related side effects.

Unless otherwise defined, all technical and scientific terms used herein have the same meaning as commonly understood by one of ordinary skill in the art to which this present application belongs. Although methods and materials similar to those described herein can be used in the practice or testing of the present application, suitable methods and materials are described below. All publications, patent applications, patents, and other references mentioned herein are incorporated in the application by reference in their entirety. In addition, the materials, methods, and examples are illustrative only and not intended to be limiting.

Non-Steroidal Anti-Inflammatory Drugs

In the instant embodiments, non-steroidal anti-inflammatory drugs are encapsulated in MVLs. The NSAIDs of the present application are acidic NSAIDs. The NSAIDs include, but are not limited to, indomethacin, sulindac, etodolac, mefenamic acid, meclofenamic acid, meclofenamate sodium, flufenamic acid, tolmetin, ketorolac, diclofenac, diclofenac sodium, propionic acid derivatives such as ibuprofen, naproxen, naproxen sodium, fenoprofen, ketoprofen, flurbiprofen, and oxaprozin, and enolic acids such as piroxicam, meloxicam, and other oxicams such as ampiroxicam, droxicam, pivoxicam, lornoxicam, cinnoxicam, sudoxicam, and tenoxicam. In particular, the NSAIDs of the instant formulations can include piroxicam (PRX). The NSAIDs of the instant formulations can also include meloxicam (MLX). The NSAIDs of the instant formulations can also include diclofenac (DCF). The NSAIDs of the instant formulations can also include ketorolac.

Multivesicular Liposomes

The instant embodiments are directed to MVLs containing one or more NSAIDs. MVLs, reported in Kim et al. (Biochim, Biophys. Acta, 728:339-348, 1983), are one of a group of large diameter synthetic membrane vesicles which include other lipid-based delivery systems such as unilamellar liposomes (Huang, Biochemistry, 8:334-352, 1969; Kim, et al., Biochim. Biophys. Acta, 646:1-10, 1981) and multilamellar liposomes (Bangham, et al., J Mol. Bio., 13:238-252, 1965). The main structural difference between multivesicular liposomes and unilamellar liposomes (also known as unilamellar vesicles), is that multivesicular liposomes contain multiple aqueous chambers per particle. The main structural difference between multivesicular liposomes and multilamellar liposomes (also known as multilamellar vesicles), is that in multivesicular liposomes the multiple aqueous chambers in multivesicular liposomes are non-concentric. The structural differences between unilamellar, multilamellar, and multivesicular liposomes are illustrated in Sankaram et al., U.S. Pat. No. 5,766,627, issued Jun. 16, 1998 and Sankaram et al., U.S. Pat. No. 6,132,766 issued Oct. 17, 2000.

The structural and functional characteristics of multivesicular liposomes are not directly predictable from current knowledge of unilamellar vesicles and multilamellar vesicles. Multivesicular liposomes have a very distinctive internal morphology, which may arise as a result of the special method employed in the manufacture. Topologically, multivesicular liposomes are defined as having multiple non-concentric chambers within each particle, resembling a "foam-like" matrix; whereas multilamellar vesicles contain multiple concentric chambers within each liposome particle, resembling the "layers of an onion."

The presence of internal membranes distributed as a network throughout multivesicular liposomes may serve to confer increased mechanical strength to the vesicle. The particles themselves can occupy a very large proportion of the total formulation volume. The packed particle volume (PPV) of MVLs which is measured in a manner analogous to a hematocrit, represents the volume of the formulation that the particles make up and can approach as high as 80%. Typically the PPV is about 50%. At 50% PPV, the multivesicular liposome formulation typically consists of less than 5% w/w lipid. Thus, the encapsulated volume is approximately 50% while having a relatively low lipid concentration. The multivesicular nature of multivesicular liposomes also indicates that, unlike for unilamellar vesicles, a single breach in the external membrane of a synthetic membrane vesicles will not result in total release of the internal aqueous contents.

Thus, multivesicular liposomes formulations consist of microscopic, spherical particles composed of numerous non-concentric aqueous chambers encapsulating the NSAID drug to be delivered. The individual chambers are separated by lipid bilayer membranes composed of synthetic duplicates of naturally occurring lipids, resulting in a delivery vehicle that is both biocompatible and biodegradable. The instant NSAID-MVL formulations provide either local site or systemic sustained delivery, and can be administered by a number of routes including subcutaneous, into muscle tissue, and into joints. Preparation of multivesicular liposomes is illustrated in Sankaram et al. (U.S. Pat. No. 5,766,627) issued on Jun. 16, 1998 and Sankaram et al. (U.S. Pat. No. 6,132,766) issued on Oct. 17, 2000.

Cyclodextrins

Cyclodextrins are chiral, toroidal-shaped molecules formed by the action of the enzyme cyclodextrin transglycosylase on starch. These cyclic oligomers contain from 6 to 12 glucose units bonded through $\alpha$-(1,4)-linkages. The three smallest homologs, $\alpha$-cyclodextrin, 3-cyclodextrin and $\gamma$-cyclodextrin are available commercially; larger homologs must be produced and isolated individually. The secondary 2- and 3-hydroxy groups line the mouth of the cyclodextrin cavity and have a staggered orientation. The primary 6-hydroxyls are at the opposite end of the molecule. The inside of the cyclodextrin cavity is relatively hydrophobic since all hydroxyls are directed toward the outside of the molecule.

Many different types of cyclodextrins could be useful in the compositions and methods of the present embodiments. Such cyclodextrins include, but are not limited to, (2,6-di-O-) ethyl-$\beta$-cyclodextrin, (2-carboxyethyl)-$\beta$-cyclodextrin sodium salt, (2-hydroxyethyl)-$\beta$-cyclodextrin, (2-hydroxypropyl)-$\alpha$-cyclodextrin, sulfobutylether-$\beta$-cyclodextrin, (2-hydroxypropyl)-$\beta$-cyclodextrin, 6-monodeoxy-6-mono-amino-$\beta$-cyclodextrin, 6-O-$\alpha$-maltosyl-$\beta$-cyclodextrin, butyl-$\beta$-cyclodextrin, butyl-$\gamma$-cyclodextrin, carboxymethyl- β-cyclodextrin, methyl-β-cyclodextrin, succinyl-α-cyclodextrin, succinyl-β-cyclodextrin, triacetyl-β-cyclodextrin, α-cyclodextrin β-cyclodextrin, and γ-cyclodextrin.

Generally, the concentration of cyclodextrin used in preparing the MVLs of the present embodiments is that which provides an adequate solubility or slows the release of pharmacologic compounds from the MVL after administration to a subject. Preferably, the cyclodextrin is present in the liposome composition in an amount of from about 10 milligrams per ml to about 400 milligrams per ml. More preferably, the amount of cyclodextrin in the liposome is about 100 mg/ml. The use of cyclodextrins in preparing MVLs is described in Kim, U.S. Pat. No. 5,759,573, issued Jun. 2, 1998.

Methods of Manufacturing

The formulations of the present embodiments employ NSAID encapsulated multivesicular liposomes (hereinafter NSAID-MVL formulations) which encapsulate and provide modulated and sustained release of the NSAIDs described above. The instant NSAID-MVL formulations are made by the following process.

A "water-in-oil" type emulsion is formed from two immiscible phases, a lipid phase and a first aqueous phase. The lipid phase is made up of at least one amphipathic lipid and at least one neutral lipid in a volatile organic solvent, and optionally cholesterol and/or cholesterol derivatives. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, stearylamine, and the like. Preferred amphipathic lipids include dioleyl phosphatidyl choline (DOPC), dierucoyl phosphatidylcholine or 1,2-dierucoyl-sn-glycero-3-phosphocholine (DEPC), and dipalmitoylphosphatidylglycerol or 1,2-dipalmitoyl-sn-glycero-3-phospho-rac-(1-glycerol) (DPPG). In certain embodiments, amphipathic lipids for the instant NSAID-MVL formulations include DOPC and DEPC in conjunction with DPPG.

Suitable neutral lipids are triglycerides, propylene glycol esters, ethylene glycol esters, and squalene. Examples of triglycerides useful in the instant formulations and methods are triolein (TO), tripalmitolein, trimyristolein, trilinolein, tributyrin, tricaproin, tricaprylin, and tricaprin. The fatty chains in the triglycerides useful in the present application can be all the same, or not all the same (mixed chain triglycerides), including all different. Both propylene glycol esters can be mixed diesters of caprylic and capric acids.

The concentrations of the amphipathic lipids, neutral lipids, and cholesterol present in the water-immiscible solvent used to make the MVLs typically range from 1-40 mM, 2-40 mM, and 0-60 mM, respectively. In some embodiments, the concentrations of the amphipathic lipids, neutral lipids, and cholesterol can be approximately 30 mM, 25 mM, and 25 mM, respectively. If a charged amphipathic lipid is included, it is generally present in a lower concentration than the zwitterionic lipid.

Many types of volatile organic solvents can be used in the present application, including ethers, esters, halogenated ethers, hydrocarbons, halohydrocarbons, or freon. For example, diethyl ether, chloroform, methylene chloride, tetrahydrofuran, ethyl acetate, and any combinations thereof are suitable for use in making the formulations.

Optionally, but highly desirable, other components are included in the lipid phase. Among these are antioxidants, antimicrobial preservatives, cholesterol or plant sterols.

In certain embodiments, the first aqueous phase can include one or more NSAIDs, pH modifiers including organic or inorganic acids and bases (for example, lysine and glutamic acid), optionally a cyclodextrin, and osmotic agents (e.g. sodium chloride, sucrose, glucose, fructose or mixtures thereof). The lipid phase and first aqueous phase are mixed by mechanical turbulence, such as through use of rotating or vibrating blades, shaking, extrusion through baffled structures or porous pipes, or by ultrasound to produce a water-in-oil emulsion. If the NSAIDs are included, the NSAIDs of the present application are encapsulated directly (directly loaded) in the first step of MVL manufacture.

The water-in-oil emulsion can then be dispersed into a second aqueous phase by means described above, to form solvent spherules suspended in the second aqueous phase, a water-in-oil-in-water emulsion is formed. The term "solvent spherules" refers to a microscopic spheroid droplet of organic solvent, within which are suspended multiple smaller droplets of aqueous solution. The second aqueous phase can contain additional components such as pH modifiers, osmotic agents and combinations thereof. Non-limiting examples of pH modifiers include lysine, arginine, and the like. Non-limiting examples of osmotic agents include monosaccharides (e.g., glucose and the like), disaccharides (e.g., sucrose and the like), and polyols (e.g., sorbitol, mannitol and the like).

The volatile organic solvent is then removed from the spherules, for instance by surface evaporation from the suspension. When the solvent is substantially or completely evaporated, MVLs are formed. Gases which can be used for the evaporation include nitrogen, argon, helium, oxygen, hydrogen, and carbon dioxide, mixtures thereof, or clean compressed air. Alternately, the volatile solvent can be removed by sparging, rotary evaporation, diafiltration or with the use of solvent selective membranes.

Methods of making the instant MVL formulations can also be found in Hartouian et al. (WO99/25319 (PCT/US98/2426), published on May 27, 1999; US 2002-0039596, published on Apr. 4, 2002), and Schutt et al. (U.S. application Ser. No. 13/083,485, published on Oct. 13, 2011), which are incorporated by references in the present application in their entireties.

As discussed above, NSAIDS can be incorporated in the MVL by their inclusion in the first aqueous phase. NSAIDs can also be incorporated in the MVL by their inclusion in the lipid phase or both the lipid and first aqueous phases.

Surprisingly, the instant NSAIDs may be remotely loaded into MVLs to give the instant NSAID-MVL formulations.

Due to the structural complexity of the MVLs, it is surprising to find that NSAIDs can be driven through a multitude of layers of membranes of the MVLs (for example, up to one hundred layers). The instant methods differ from Hwang et al., discussed above. For example, in the instant embodiments, the MVLs are used as the recipient for the NSAIDs, and only pH gradients are used. Further, a gradient of low pH outside the MVLs to high pH inside the MVLs is present to drive the NSAIDs into the MVLs. Moreover, the instant embodiments do not rely on the use of calcium acetate or sodium acetate or a precipitation mechanism. Once blank MVLs (containing no active compound) are formed by the methods described above, NSAID-MVL formulations can be prepared by adding a drug-containing solution to the suspension of MVLs. In such a case, a gradient of low pH outside the MVLs to high pH inside the MVL is present to drive the NSAID into the MVLs.

Also, remote loading can be driven by precipitation of the NSAIDs once inside the MVLs. In such a case, a cation would be included in the blank MVLs which would form a low solubility salt with the NSAIDs. Cations can include, but are not limited to, sodium, calcium, magnesium, aluminum and the like.

Methods of Administration

Current modalities of post-operative analgesia include wound infiltration with local anesthetics combined with the systemic administration of NSAIDs and opioids. Opioid medications, which have considerable drawbacks including time and resources required for monitoring and treating opioid-related side effects. A reduction in the use of post-operative opioids is desirable to decrease the incidence and severity of opioid-induced adverse effects, such as respiratory depression, nausea, vomiting, constipation, somnolence, pruritus, and urinary retention. The instant embodiments provide extended release formulations of NSAIDs to the wound site, thus avoiding the use of systemic opioids.

In any of the embodiments, the instant NSAID-MVL formulations can be administered by bolus injection, e.g., subcutaneous bolus injection, intraarticular bolus injection, intramuscular bolus injection, intradermal bolus injection and the like. In any of the embodiments, administration can be by infusion, e.g., subcutaneous infusion, intraarticular infusion, intramuscular infusion, intradermal infusion, and the like. In any of the embodiments, administration can be direct wound infiltration by local injection into the wound margin or instillation into the incision wound, or a combination thereof. The NSAID-MVL formulations can also be administered by other routes of administration to treat local inflammation or pain including, but not limited to, topical, ocular, intraocular, nasal, and otic delivery.

Administration of the instant NSAID-MVL formulations is accomplished using standard methods and devices, e.g., pens, injector systems, needle and syringe, a subcutaneous injection port delivery system, and the like. See, e.g., Hall et al., U.S. Pat. No. 3,547,119, issued Dec. 15, 1970; Konopka et al., U.S. Pat. No. 4,755,173, issued Jul. 5, 1988; Yates, U.S. Pat. No. 4,531,937, issued Jul. 30, 1985; Gerard, U.S. Pat. No. 4,311,137, issued Jan. 19, 1982; and Fischell et al., U.S. Pat. No. 6,017,328 issued Jan. 25, 2000, each of which is herein incorporated by reference in their entirety.

In preferred embodiments, the NSAID-MVL formulations are administered subcutaneously, intramuscularly, or intraarticularly. Such administration can occur at about 1 to about 7 day intervals at a dose of from about 7.5 mg to about 200 mg for systemic use, and about 0.1 mg to about 10 mg for intraarticular use. Exact dosages will vary depending on patient factors such as age, sex, general condition, and the like. Those of skill in the art can readily take these factors into account and use them to establish effective therapeutic concentrations without resort to undue experimentation.

For systemic administration, the amount of DCF administered per day is preferably between about 150 mg and about 200 mg. The amount of PRX administered per day is preferably about 20 mg. The amount of MLX administered per day is preferably between about 7.5 mg and about 15 mg.

For intraarticular administration, the amount of DCF, PRX, and MLX administered per dose will be significantly lower than for subcutaneous administration. For instance, the amount of DCF administered per day can be between about 0.5 mg and about 2.0 mg. The amount of PRX administered per day can be about 0.2 mg. The amount of MLX administered per day is preferably between about 0.075 mg and about 0.15 mg.

In some embodiments, the NSAID-MVL formulations optionally include a pharmaceutically acceptable carrier. Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, a tonicity agent such as sucrose or saline, preservatives such as benzyl alcohol, if needed, and buffers. Useful solvents include, for example, water and aqueous alcohols, glycols, and carbonate esters such as diethyl carbonate.

Injectable suspension compositions require a liquid suspending medium, with or without adjuvants, as a vehicle. The suspending medium can be, for example, aqueous solutions of sodium chloride, sucrose, polyvinylpyrrolidone, polyethylene glycol, or combinations of the above.

Suitable physiologically acceptable adjuvants are necessary to keep the compound suspended in suspension compositions. The adjuvants may be chosen from among thickeners such as carboxymethylcellulose, polyvinylpyrrolidone, gelatin and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

As used herein, the term "subject" includes animals and humans. In a preferred embodiment, the subject is a human.

Non-Limiting Disclosure and Incorporation by Reference

While certain therapeutic agents, compositions and methods of the present invention have been described with specificity in accordance with certain embodiments, the following examples serve only to illustrate the compositions and methods of the invention and are not intended to limit the same.

EXAMPLES

Example 1—Remote Loading

Remote-loaded NSAID-MVL formulations were manufactured as follows: blank MVL formulations were prepared in a manner similar to that reported in Kim et al. (*Biochim. Biophys. Acta*, 728:339-348, 1983). MVLs were manufactured wherein an aqueous solution, adjusted to specific pH, and in some cases contained cyclodextrins (Kim, U.S. Pat. No. 5,759,573, issued Jun. 2, 1998), were emulsified with a lipid-containing chloroform solution to form a water-in-oil (W/O) emulsion. The W/O emulsion was then emulsified in a second aqueous solution to produce a W/O/W emulsion. The W/O/W emulsion was then stirred at 37° C. under a nitrogen stream to remove the chloroform by evaporation. The resulting blank MVLs were centrifuged, and the supernatant was replaced with normal saline. After washing the blank MVLs were diluted into normal saline to yield a product with approximately a 50% packed particle volume (PPV). PPV is the fraction of the total formulation volume taken up by the MVL particles.

The NSAID compounds were then remote-loaded into the blank MVLs by incubating the pH-adjusted NSAID solutions described below in Tables 1, 2 and 3 with the blank MVL particle suspensions, under gentle agitation. Tables 1, 2, and 3 are summaries of the components and results for the NSAID-MVL formulations wherein the NSAIDs are PRX, DCF, and MLX, respectively. After the NSAIDs had partitioned into the blank MVLs, the suspensions were washed in normal saline to remove unencapsulated, or free, NSAID.

Further, the MVL formulations of Table 2, above, were manufactured using an inside:outside pH gradient with a magnitude of about 1.5. The inner and outer solutions were adjusted to a higher pH, which provided improved DCF solubility. The loading solution contained 4.2 mg/mL DCF in NaHPO$_4$, pH 7.5, and the internal solution contained lysine-glutamic acid, pH 9-9.2. Using these reduced gradient-higher pH conditions, significantly higher DCF recoveries than those described in Hwang et al., above, of 17-61% (see Table 2) were obtained.

NSAID recovery in the instant MVLs was analyzed by first lysing the NSAID-containing MVL by mixing one part suspension with three parts isopropyl alcohol, vortexing to dissolution, and then further diluting with six parts of the RP-HPLC (reverse phase high pressure liquid chromatography) running buffer as described in the United States Pharmacopeia method for each NSAID.

TABLE 1

Solution compositions and final product attributes for PRX-MVL Formulations

| | Component | Formulation 1 | Formulation 2 | Formulation 3 | Formulation 4 |
|---|---|---|---|---|---|
| Placebo 1st Aqueous Solution | Lysine, mM | 115 | 199 | 94 | 99 |
| | Glutamic acid, mM | 58 | 100 | 47 | 40 |
| | HPB-Cyclodextrin, % | 10 | 0 | 13 | 13 |
| | pH | 9.1 | 9.1 | 9.0 | 9.2 |
| | Osmolality, mOsm/kg | 295 | 297 | 296 | 298 |
| PRX Loading Solution | Piroxicam, mg/mL | 4.6 | 4.6 | 4.6 | 4.6 |
| | NaHPO$_4$, mM | 121 | 121 | 121 | 121 |
| | pH | 7.6 | 7.6 | 7.6 | 7.6 |
| | Osmolality, mOsm/kg | 300 | 300 | 300 | 300 |
| Lipid Combo | Tricaprylin, mM | 40 | 40 | 40 | 40 |
| | Cholesterol, mM | 40 | 40 | 40 | 40 |
| | DPPG-Na+, mM | 13 | 13 | 13 | 13 |
| | DEPC, mM | 26.4 | 26.4 | 26.4 | 26.4 |
| 2nd Aqueous solution | Lysine, mM | 20 | 20 | 20 | 20 |
| | Sorbitol, % | 4.7 | 4.7 | 4.7 | 4.7 |
| | pH | 10 | 10 | 10 | 10 |
| | Osmolality, mOsm/kg | 291 | 291 | 291 | 291 |
| Particle Size Distribution (PSD) | d10 | 6.4 | 11.8 | 6.3 | 6.1 |
| | d50 | 13.2 | 20.4 | 12.7 | 12.3 |
| | d90 | 25.5 | 34.1 | 24.1 | 23.5 |
| Analytical Results | Total Potency, mg/mL | 4.9 | 3.9 | 4.6 | 5.5 |
| | PRX Recovery % | 54.3 | 44.7 | 51.3 | 61.8 |
| | % Free NSAID | 0.4 | 1.2 | 0.4 | 0.4 |
| | PPV % | 54.2 | 54.9 | 53.5 | 52.8 |

TABLE 2

Solution compositions and final product attributes for DCF-MVL Formulations

| | Component | Formulation 5 | Formulation 6 | Formulation 7 | Formulation 8 |
|---|---|---|---|---|---|
| Placebo 1st Aqueous Solution | Lysine, mM | 115 | 78 | 94 | 99 |
| | Glutamic acid, mM | 58 | 39 | 47 | 40 |
| | HPB-Cyclodextrin, % | 10 | 15 | 13 | 13 |
| | pH | 9.1 | 9.0 | 9.0 | 9.2 |
| | Osmolality, mOsm/kg | 295 | 296 | 296 | 298 |
| DCF Loading Solution | Diclofenac, mg/mL | 4.2 | 4.2 | 4.2 | 4.2 |
| | NaHPO$_4$, mM | 121 | 121 | 121 | 121 |
| | pH | 7.5 | 7.5 | 7.5 | 7.5 |
| | Osmolality, mOsm/kg | 302 | 302 | 302 | 302 |

TABLE 2-continued

Solution compositions and final product attributes for DCF-MVL Formulations

| | Component | Formulation 5 | Formulation 6 | Formulation 7 | Formulation 8 |
|---|---|---|---|---|---|
| Lipid Combo | Tricaprylin, mM | 40 | 40 | 40 | 40 |
| | Cholesterol, mM | 40 | 40 | 40 | 40 |
| | DPPG-Na+, mM | 13 | 13 | 13 | 13 |
| | DEPC, mM | 26.4 | 26.4 | 26.4 | 26.4 |
| 2nd Aqueous solution | Lysine, mM | 20 | 20 | 20 | 20 |
| | Sorbitol, % | 4.7 | 4.7 | 4.7 | 4.7 |
| | pH | 10 | 10 | 10 | 10 |
| | Osmolality, mOsm/kg | 291 | 291 | 291 | 291 |
| Particle Size Distribution | d10 | 6.4 | 5.6 | 5.6 | 6.6 |
| | d50 | 11.9 | 10.6 | 11.0 | 13.0 |
| | d90 | 21.0 | 18.9 | 19.6 | 24.3 |
| Analytical Results | DCF Recovery, % | 17 | 26 | 29 | 61 |
| | Total Potency, mg/mL | 5.8 | 4.9 | 5.4 | 6.9 |
| | % Free NSAID | 2.6 | 1.9 | 1.6 | 0.8 |
| | PPV % | 47.2 | 47.9 | 46.5 | 46.5 |

TABLE 3

Solution compositions and final product attributes for MLX-MVL Formulations

| | Component | Formulation 9 | Formulation 10 | Formulation 11 | Formulation 12 | Formulation 13 | Formulation 14 |
|---|---|---|---|---|---|---|---|
| Placebo 1st Aqueous Solution | Lysine, mM | 40 | 40 | 40 | 40 | 115 | 40 |
| | Glutamic acid, mM | 20 | 20 | 20 | 20 | 58 | 20 |
| | HPB-CD, % | 20 | 10 | 9.5 (SBE)* | 10 | 10 | 20 |
| | pH | 9.0 | 9.0 | 9.1 | 9.0 | 9.1 | 9.0 |
| | Osmolality, mOsm/kg | 301 | 292 | 302 | 301 | 298 | 297 |
| MLX Loading Solution | Meloxicam, mg/mL | 6 | 6 | 6 | 4.8 | 4.8 | 4.8 |
| | $NaHPO_4$, mM | 126 | 126 | 126 | 120 | 120 | 120 |
| | pH | 8.0 | 8.0 | 8.0 | 8.0 | 8.0 | 8.0 |
| | Osmolality, mOsm/kg | 304 | 304 | 304 | 295 | 295 | 295 |
| Lipid Combo | Tricaprylin, mM | 40 | 40 | 40 | 40 | 40 | 40 |
| | Cholesterol, mM | 40 | 40 | 40 | 40 | 40 | 40 |
| | DPPG-Na$^+$, mM | 11.2 | 11.2 | 11.2 | 11.2 | 11.2 | 11.2 |
| | DEPC, mM | 26.4 | 26.4 | 26.4 | 26.4 | 26.4 | 26.4 |
| 2nd Aqueous solution | Lysine, mM | 20 | 20 | 20 | 20 | 20 | 20 |
| | Sorbitol, % | 4.8 | 4.8 | 4.8 | 4.8 | 4.8 | 4.8 |
| | pH | 10 | 10 | 10 | 10 | 10 | 10 |
| | Osmolality, mOsm/kg | 291 | 291 | 291 | 291 | 291 | 291 |
| Particle Size Distribution | d10 | 6.1 | 6.3 | 9.7 | 6.8 | 7.6 | 6.7 |
| | d50 | 12.3 | 13.1 | 18.3 | 14.1 | 16.0 | 13.8 |
| | d90 | 24.2 | 24.9 | 33.9 | 28.3 | 46..0 | 31.7 |
| Analytical Results | Total Potency, mg/mL | 3.4 | 2.9 | 2.2 | 2.7 | 3.4 | 3.2 |
| | MLX Recovery % | 56.4 | 49.3 | 37.4 | 55.4 | 71.2 | 67.1 |
| | % Free | 0.8 | 1.0 | 2.8 | 0.9 | 1.1 | 1.0 |
| | PPV % | 55 | 55 | 56 | 52 | 51 | 51 |
| | pH | 7.1 | 7.0 | 7.0 | 6.9 | 7.5 | 7.3 |

*SBE means sulfobutylether β-cyclodextrin

As shown in Table 4 below, in formulations containing 182 mM lysine/glutamic acid (+5 mM Calcium Acetate (Ca(OAc)$_2$)), DCF loading was higher in formulations comprised of longer-chain phosphatidylcholine (83% vs. 0% recovery in DEPC versus dioleylphosphatidylcholine (DOPC)). Formulations containing lysine/glutamic acid at higher concentration (182 vs. 93 mM) and increased pH gradient (9.0 vs. 7.5) had improved DCF loading (78% v 43% recovery). In 300 mM lysine/glutamic acid formulations, increasing the DCF loading concentration to 4.6 mg/ml resulted in batch failure. In 100 mM lysine/glutamic acid formulations, encapsulation and recovery decreased with increasing DCF concentration in the loading solution. Encapsulation and recovery were improved significantly by adding between about 2 to about 10% HPB-CD. In some embodiments 2% HPB-CD can be added. In further embodiments 3% HPB-CD can be added. Likewise, 4% HPB-CD can be added. In additional embodiments, between about 5 and about 9% HPB-CD can be added. In further embodiments, between about 6 to about 15% HPB-CD can be added. In further embodiments, between about 2 to about 15% HPB-CD can be added.

In lysine/glutamic acid only formulations, addition of 15% HPB-CD with osmolarity adjustment enabled an increase in the DCF encapsulation of the particles to 4.6 mg/mL (67% recovery). HPB-CD was not required to achieve high encapsulation (7.2 mg/mL) with other NSAIDS (i.e. PRX). In HPB-CD-containing lysine/glutamic acid formulations, higher-concentration buffer conditions still provided improved encapsulation and recovery.

TABLE 4

Impact of phosphatidylcholine (PC) chain length, buffer concentration, and HPB-CD on NSAID encapsulation.

| Drug | Formulation | Blank particle composition | Loading solution[a] drug conc, mg/mL | Loading Solution pH | PC | Final drug potency, mg/mL | % Recovery |
|---|---|---|---|---|---|---|---|
| DCF | A | 5 mM Ca(OAc)$_2$, 182 mM LysGlut, pH 9.0 | 0.52 | 7.0 | DEPC | 0.43 | 83 |
| DCF | B | 5 mM Ca(OAc)$_2$, 182 mM LysGlut, pH 9.0 | 0.65 | 7.0 | DOPC | na | failed |
| DCF | C | 5 mM Ca(OAc)$_2$, 182 mM LysGlut, pH 9.0 | 1.1 | 6.9 | DEPC | 0.85 | 78 |
| DCF | D | 5 mM Ca(OAc)$_2$, 93 mM LysGlut, pH 7.5 | 1.1 | 6.9 | DEPC | 0.46 | 43 |
| DCF | E | 300 mM LysGlut, 0% HBP-CD, pH 9 | 4.6 | 7.5 | DEPC | na | Failed |
| DCF | F | 100 mM LysGlut, 2% HBP-CD, pH 9 | 1.1 | 7.0 | DEPC | 0.9 | 83 |
| DCF | G | 100 mM LysGlut, 10% HBP-CD, pH 9 | 1.1 | 7.0 | DEPC | 1.0 | 96 |
| DCF | H | 100 mM LysGlut, 2% HBP-CD, pH 9 | 3.2 | 7.4 | DEPC | 2.0 | 62 |
| DCF | I | 100 mM LysGlut, 10% HBP-CD, pH 9 | 3.2 | 7.4 | DEPC | 2.3 | 72 |
| DCF | J | 117 mM LysGlut, 15% HBP-CD, pH 9 | 4.6 | 7.5 | DEPC | 4.6 | 67 |
| DCF | K | 60 mM LysGlut, 15% HBP-CD, pH 9 | 4.6 | 7.5 | DEPC | 3.1 | 46 |
| PRX | L | 300 mM LysGlut, 0% HBP-CD, pH 9 | 4.5 | 7.5 | DEPC | 7.2 | 80 |
| PRX | M | 173 mM LysGlut, 10% HBP-CD, pH 9 | 4.5 | 7.5 | DEPC | 5.0 | 55 |

[a]Drug loading solutions were prepared in 150 mM sodium phosphate, unless otherwise indicated.

In addition to the formulations manufactured using lysine-glutamic acid solutions, blank MVLs were also manufactured using lysine-acetic acid solutions (as summarized in Table 5 below). Table 5 is a summary of the components and results for DCF-MVL formulations remote loaded using lysine and acetic acid. A low internal pH blank MVL was also investigated. The pH of the blank MVL was as low as 2.1 units below the loading solution. A significantly lower concentration of lysine-acetic acid solution was employed (10-25 mM versus 120-150 mM calcium or sodium acetate as reported by Hwang). This approach of employing lower concentration of lysine-acetic acid solution led to NSAID loading through the use of a membrane permeable acid such as acetic acid. Recovery in NSAID-MVL formulations was higher in solutions with higher pH as exemplified below in Table 5.

TABLE 5

DCF-MVL particles remote-loaded using lysine and acetic acid

| | Component | Formulation 15 | Formulation 16 | Formulation 17 |
|---|---|---|---|---|
| Blank Particles | Lysine, mM | 25 | 25 | 25 |
| | Acetic acid, mM | 20 | 20 | 20 |
| | Internal particle pH | 4.7 | 7.7 | 8.7 |
| DCF Loading Solution | DCF-Na, mg/mL | 1.0 | 1.0 | 1.0 |
| | NaPO$_4$, mM | 150 | 150 | 150 |
| | pH | 6.9 | 6.9 | 6.9 |
| | pH gradient (in:out) | −2.2 | 0.8 | 1.8 |
| Lipid Solution | Tricaprylin, mM | 10 | 10 | 10 |
| | Cholesterol, mM | 25 | 25 | 25 |
| | DPPG-Na+, mM | 5.6 | 5.6 | 5.6 |
| | DEPC, mM | 26.4 | 26.4 | 26.4 |
| Second Aqueous solution | Lysine, mM | 45 | 45 | 45 |
| | Acetic acid, mM | 20 | 20 | 20 |
| | Sorbitol, % | 4.2 | 4.2 | 4.2 |
| | pH | 9.2 | 9.2 | 9.2 |
| | Osmolality, mOsm/kg | 301 | 301 | 301 |
| Wash/Storage solution | Lysine, mM | 20 | 20 | 20 |
| | Acetic acid, mM | 40 | 20 | 20 |
| | pH | 4.6 | 7.0 | 8.7 |
| | Osmolarity, mOsm/kg | 288 | 288 | 290 |
| Final Product | DCF Recovery, % | 36 | 74 | 71 |
| | Total Potency, mg/mL | 0.34 | 0.70 | 0.67 |
| | % Free NSAID | 5.1 | 4.5 | 3.5 |
| | PPV % | 45.1 | 46.5 | 46.5 |

Example 2—Direct Loading

Direct-loaded NSAID-MVL formulations were manufactured as follows: MVLs containing an NSAID were produced by traditional direct-loading methods wherein the active (NSAID) drug is dissolved in the first aqueous solution and then encapsulated as described in Hartouian et al., (WO99/25319 (PCT/US98/2426), published on May 27, 1999, and US 2002-0039596, published on Apr. 4, 2002). As shown in Table 6, this approach yielded MVL particles with NSAID encapsulated at either low efficiencies or not at all.

TABLE 6

Direct loading of NSAIDs into MVLs

| Drug | Formulation | 1st Aqueous | Lipid composition (PC) | Potency, mg/mL | % Recovery |
|---|---|---|---|---|---|
| PRX | N | 2 mg/mL PRX in 70 mM LysGlut, pH 8.3 | DEPC | 0.021 | 2 |
| DCF | O | 10 mg/mL DCF in 50 mM MegluminePO$_4$, pH 7.5 | DOPC | 0 | failed[a] |
| DCF | P | 4 mg/mL DCF in 50 mM MegluminePO4, pH 7.5 | DOPC/DEPC | 0 | failed[a] |
| DCF | Q | 1 mg/mL DCF in 20 mM PBS, pH 6.5 | DOPC/DEPC | 0 | 0 |
| DCF | R | 1 mg/mL DCF*Na in 293 mM ArginineGlut, 3% HBP-CD, pH 9 | DOPC | 0 | failed[a] |
| DCF | S | 0.2 mg/mL DCF*Na in 149 mMLysGlut, pH 8.5 | DEPC | 0 | 0 |
| DCF | T | 1 mg/mL DCF*Na in 149 mMLysGlut, pH 8.5 | DEPC | 0 | 0 |
| DCF | U | 1 mg/mL DCF*Na in 100 mM LysGlut, 20% HBP-CD, pH 9 | DEPC | 0.032 | <6 |

[a]Failed indicates that MVL particles were not formed or were grossly aggregated.

MVLs containing DCF were also produced by placing NSAID in either the lipid solution alone (at concentrations up to the solubility in the solvent), or portions of the NSAID in both the first aqueous solution and the lipid solution (see Table 7 below). This approach was useful for the manufacture of MVLs, often producing final NSAID concentrations between 0.1 and 1 mg/mL.

TABLE 7

DCF partitioning from lipid solution (or lipid and aqueous phases) into MVLs

| Drug | Formulation | 1st Aqueous ± DCF | DCF conc. (mg/mL) in Lipid solution | Potency, mg/mL | % Recovery |
|---|---|---|---|---|---|
| DCF | V | 148 mM LysineGlutamate, pH 8.5 | 2 mg/mL DCF-A in DEPC lipid solution | 0 | 0 |
| DCF | W | 148 mM LysineGlutamate, pH 8.5 | 8 mg/mL DCF-A in DEPC lipid solution | 0.04 | 1.1 |
| DCF | X | 149 mM LysineGlutamate, pH 8.5 | 20 mg/mL DCF-A in DEPC lipid solution | 0.14 | 1.2 |
| DCF | Y | 148 mM LysineGlutamate, pH 8.5 | 16 mg/mL DCF-A in DEPC lipid solution | 0.18 | 2.9 |
| DCF | Z | 0.5 mg/mL DCF*Na in 148 mM LysineGlutamate, pH 8.5 | 16 mg/mL DCF-A in DEPC lipid solution | 0.18 | 2.8 |
| DCF | AA | 4 mg/mL DCF free acid (DCF-A) in 26 mM Lysine, pH 9.1 | 20 mg/mL DCF-A in DEPC lipid solution | 0.22 | 1.5 |
| DCF | BB | 3.8 mg/mL DCF-A in 29 mM LysineGlutamate, pH 9 | 20 mg/mL DCF-A in DEPC lipid solution | 0.78 | 6.6 |

Example 3—Stability

The stability of the instant NSAID-MVL formulations (stored in Type I borosilicate glass vials, sealed with ETFE-faced grey butyl stoppers) is acceptable by industry standards. Stability data for the Formulations in Tables 1 and 2 above are shown in Tables 8 and 9 below. Properties assessed included drug content ("Total") and percent of unencapsulated drug (% free) by RP-HPLC methods, packed particle volume ("PPV") which is assessed in a manner analogous to a hematocrit, and particle size which is assessed by laser light scattering. At refrigerated temperatures (5° C.), no significant changes are observed through 3 months.

TABLE 8

Storage stability for DCF-MVL at 5° C.

| Formulation # | Brief Component Description | Yield | Incub'n Time (d) | Total [DCF] (mg/mL) | % PPV | % Free DCF | d10 | d50 | d90 | Sup pH | Int pH |
|---|---|---|---|---|---|---|---|---|---|---|---|
| Formulation 5 | (10% HPB-CD, pH 9.0) 115:58 Lysine:Glut acid | 17.2 | 0 | 5.82 | 47.2 | 2.58 | 6.4 | 11.9 | 21.0 | 6.8 | 8.38 |
| | | | 30 | 5.74 | 43.0 | 6.01 | 6.6 | 13.0 | 24.0 | 7.53 | 8.34 |
| | | | 97 | 5.91 | 42.9 | — | — | — | — | 7.15 | 8.31 |
| Formulation 6 | (15% HPB-CD, pH 9.0) 78:39 Lysine:Glut acid | 26.0 | 0 | 4.90 | 47.9 | 1.92 | 5.6 | 10.6 | 18.9 | 6.75 | 8.15 |
| | | | 30 | 4.60 | 41.0 | 3.87 | 5.7 | 11.0 | 19.6 | 7.28 | 8.08 |
| | | | 97 | 5.10 | 45.0 | 2.78 | — | — | — | 7.45 | 8.09 |
| Formulation 7 | (13% HPB-CD, pH 9.0) 94:47 Lysine:Glut acid | 28.8 | 0 | 5.39 | 46.5 | 1.60 | 5.6 | 11.0 | 19.6 | 6.64 | 8.20 |
| | | | 30 | 5.26 | 42.0 | 4.24 | 5.7 | 10.9 | 19.4 | 7.45 | 8.21 |
| | | | 97 | 5.65 | 44.3 | 2.99 | — | — | — | 7.09 | 8.18 |
| Formulation 8 | (13% HPB-CD, pH 9.2) 99:40 Lysine:Glut acid | 61.3 | 0 | 6.90 | 46.5 | 0.83 | 6.6 | 13.0 | 24.3 | 6.50 | 8.21 |
| | | | 30 | 6.69 | 42.0 | 4.73 | 6.5 | 12.2 | 21.4 | 7.44 | 8.32 |
| | | | 97 | 6.86 | 43.6 | 3.93 | — | — | — | 6.95 | 8.23 |

TABLE 9

Storage stability for PRX-MVL at 5° C.

| Formulation | Brief Component Description | Yield | Incub'n Temp | Incub'n Time (d) | Total [PRX] (mg/mL) | % PPV | % Free PRX | Int pH | d10 | d50 | d90 |
|---|---|---|---|---|---|---|---|---|---|---|---|
| Formulation 1 | (10% HPB-CD, pH 9.0) 115:58 mM Lysine:Glut acid | 54.3% | 5° C. | 0 | 4.94 | 54.2 | 0.42 | 8.27 | 6.4 | 13.2 | 25.5 |
| | | | 5° C. | 30 | 5.14 | 52.0 | 2.03 | 8.23 | 6.5 | 13.5 | 26.0 |
| | | | 5° C. | 97 | 4.86 | 55.7 | 2.29 | 8.24 | — | — | — |
| Formulation 2 | (Buffer only, pH 9.0) 199:100 mM Lysine:Glut acid | 44.7% | 5° C. | 0 | 3.91 | 54.9 | 1.22 | 8.69 | 11.8 | 20.4 | 34.1 |
| | | | 5° C. | 30 | 4.06 | 48.0 | 5.56 | 8.69 | 12.3 | 21.1 | 35.3 |
| | | | 5° C. | 97 | 3.78 | 52.1 | 6.06 | 8.69 | — | — | — |
| Formulation 3 | (13% HPB-CD, pH 9.0) 94:47 mM Lysine:Glut acid | 51.3% | 5° C. | 0 | 4.60 | 53.5 | 0.37 | 8.14 | 6.3 | 12.7 | 24.1 |
| | | | 5° C. | 30 | 4.79 | 51.0 | 2.15 | 8.09 | 6.5 | 13.0 | 24.8 |
| | | | 5° C. | 97 | 4.44 | 52.9 | 2.93 | 8.10 | — | — | — |
| Formulation 4 | (13% HPB-CD, pH 9.2) 99:40 mM Lysine:Glut acid | 61.8% | 5° C. | 0 | 5.45 | 52.8 | 0.36 | 8.32 | 6.1 | 12.3 | 23.5 |
| | | | 5° C. | 30 | 5.73 | 50.0 | 2.20 | 8.30 | 6.2 | 12.4 | 23.5 |
| | | | 5° C. | 97 | 5.62 | 52.1 | 1.92 | 8.28 | — | — | — |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A process for preparing multivesicular liposomal formulations, the process comprising:
   providing a first emulsion comprising at least one non-steroidal anti-inflammatory drug selected from the group consisting of piroxicam, and meloxicam by mixing a first aqueous phase comprising the at least one non-steroidal anti-inflammatory drug and one or more pH modifiers and a volatile water-immiscible solvent phase, wherein said solvent phase comprises at least one amphipathic lipid and at least one neutral lipid;
   mixing and emulsifying said first emulsion and a second aqueous phase to provide a second emulsion, said second emulsion comprising a continuous aqueous phase; and
   removing the volatile water-immiscible solvent from the second emulsion to form a composition of multivesicular liposomal particles encapsulating at least one non-steroidal anti-inflammatory drug in the first aqueous phase, wherein the multivesicular liposomes are characterized by an internal pH of about 7 or higher.

2. The process of claim 1, wherein the multivesicular liposomes further comprise a pH modifier in the second aqueous phase.

3. The process of claim 1, wherein the pH modifier of the first aqueous phase comprises lysine or glutamic acid, or a combination thereof.

4. The process of claim 1, wherein the pH modifier of the first aqueous phase comprises an inorganic acid.

5. The process of claim 1, wherein the pH modifier of the first aqueous phase comprises an organic base.

6. The process of claim 1, wherein the pH modifier of the first aqueous phase comprises an inorganic base.

7. The process of claim 1, wherein the non-steroidal anti-inflammatory drug is piroxicam.

8. The process of claim 1, wherein the non-steroidal anti-inflammatory drug is meloxicam.

9. The process of claim 1, wherein the pH modifier of the first aqueous phase comprises an organic acid.

10. The process of claim 1, wherein at least one amphipathic lipid is selected from zwitterionic phospholipids, anionic amphipathic phospholipids, cationic amphipathic lipids, or combinations thereof.

11. The process of claim 1, wherein at least one amphipathic lipid is selected from phosphatidylcholines, phosphatidylethanolamines, sphingomyelins, lysophosphatidylcholines, lysophosphatidylethanolamines, or combinations thereof.

12. The process of claim 1, wherein at least one amphipathic lipid is selected from phosphatidylglycerols, phosphatidylserines, phosphatidylinositols, phosphatidic acids, cardiolipins, or combinations thereof.

13. The process of claim 1, wherein at least one amphipathic lipid is selected from acyl trimethylammonium propanes, diacyl dimethylammonium propanes, stearylamine, or combinations thereof.

14. The process of claim 1, wherein at least one amphipathic lipid is selected from dioleyl phosphatidyl choline (DOPC), dierucoyl phosphatidylcholine or 1,2-dierucoyl-sn-glycero-3-phosphocholine (DEPC), dipalmitoylphosphatidylglycerol or 1,2-dipalmitoyl-sn-glycero-3-phospho-rac-(1-glycerol) (DPPG), or combinations thereof.

15. The process of claim 1, wherein at least one neutral lipid is selected from triglycerides, propylene glycol esters, ethylene glycol esters, squalene, or combinations thereof.

16. The process of claim 1, wherein at least one neutral lipid is selected from tricaprylin, or triolein or combination of the two.

17. The process of claim 1, wherein the multivesicular liposomes are characterized by an internal pH of about 8 to about 9.

18. The process of claim 7, wherein the multivesicular liposomes are characterized by an internal pH of about 8 to about 9.

19. The process of claim 8, wherein the multivesicular liposomes are characterized by an internal pH of about 8 to about 9.

* * * * *